(12) United States Patent
Ishii et al.

(10) Patent No.: US 7,048,834 B2
(45) Date of Patent: May 23, 2006

(54) METHOD FOR PURIFICATION OF ACRYLIC ACID

(75) Inventors: Yoshitake Ishii, Hineji (JP); Kouji Ueno, Hineji (JP); Kazuhiko Sakamoto, Hineji (JP); Sei Nakahara, Hineji (JP); Masatoshi Ueoka, Hineji (JP); Tetsuji Mitsumoto, Hineji (JP); Takeshi Nishimura, Hineji (JP); Mamoru Takamura, Takasago (JP); Hisao Nakama, Ibo-gun (JP)

(73) Assignee: Nippon Shokubai Co., Ltd., Osaka (JP)

( * ) Notice: Subject to any disclaimer, the term of this patent is extended or adjusted under 35 U.S.C. 154(b) by 676 days.

(21) Appl. No.: 09/745,896

(22) Filed: Dec. 21, 2000

(65) Prior Publication Data

US 2001/0004960 A1 Jun. 28, 2001

(30) Foreign Application Priority Data

Dec. 22, 1999 (JP) .................................. 11-365153

(51) Int. Cl.
B01D 3/34 (2006.01)
B01D 3/42 (2006.01)
C07C 51/44 (2006.01)
C07C 51/487 (2006.01)
C07C 57/07 (2006.01)

(52) U.S. Cl. ................... 203/3; 203/8; 203/38; 203/59; 562/600

(58) Field of Classification Search .................. 203/6, 203/8, 38, 60, 3, 29, 59; 562/600
See application file for complete search history.

(56) References Cited

U.S. PATENT DOCUMENTS

| 5,482,597 | A | * | 1/1996 | Herbst et al. ................. 203/38 |
| 5,571,386 | A | * | 11/1996 | Bauer et al. ................. 203/38 |
| 5,746,892 | A | * | 5/1998 | Bauer et al. ................. 203/38 |
| 5,759,358 | A | | 6/1998 | Bauer, Jr. et al. |
| 6,179,966 | B1 | * | 1/2001 | Shimizu et al. ............... 203/15 |
| 6,207,022 | B1 | * | 3/2001 | Dockner et al. .............. 203/38 |
| 6,228,227 | B1 | * | 5/2001 | Herbst et al. ................. 203/59 |
| 6,352,619 | B1 | * | 3/2002 | Fauconet et al. .............. 203/8 |
| 6,458,989 | B1 | * | 10/2002 | Aichinger et al. ........... 560/218 |
| 6,787,001 | B1 | * | 9/2004 | Sakamoto et al. ............. 203/2 |

FOREIGN PATENT DOCUMENTS

| FR | 2 753 445 A1 | 3/1998 |
| GB | 2 285 046 A | 6/1995 |
| JP | 7-228548 A | 8/1995 |
| JP | 9-316027 A | 12/1997 |

* cited by examiner

Primary Examiner—Virginia Manoharan

(57) ABSTRACT

The present invention provides an industrially easy and economical method for purification of acrylic acid which enables to efficiently eliminate impurities from a crude acrylic acid containing aldehydes as the impurities while the formation of acrylic acid polymer is inhibited. The method for purification of acrylic acid includes the step of distilling a crude acrylic acid which is charged with an aldehyde treatment chemical, wherein the concentration ratio of furfural to acrolein by weight in the crude acrylic acid is adjusted so as to satisfy the following equation:

(furfural concentration by weight)/(acrolein concentration by weight)≦100.

10 Claims, 7 Drawing Sheets

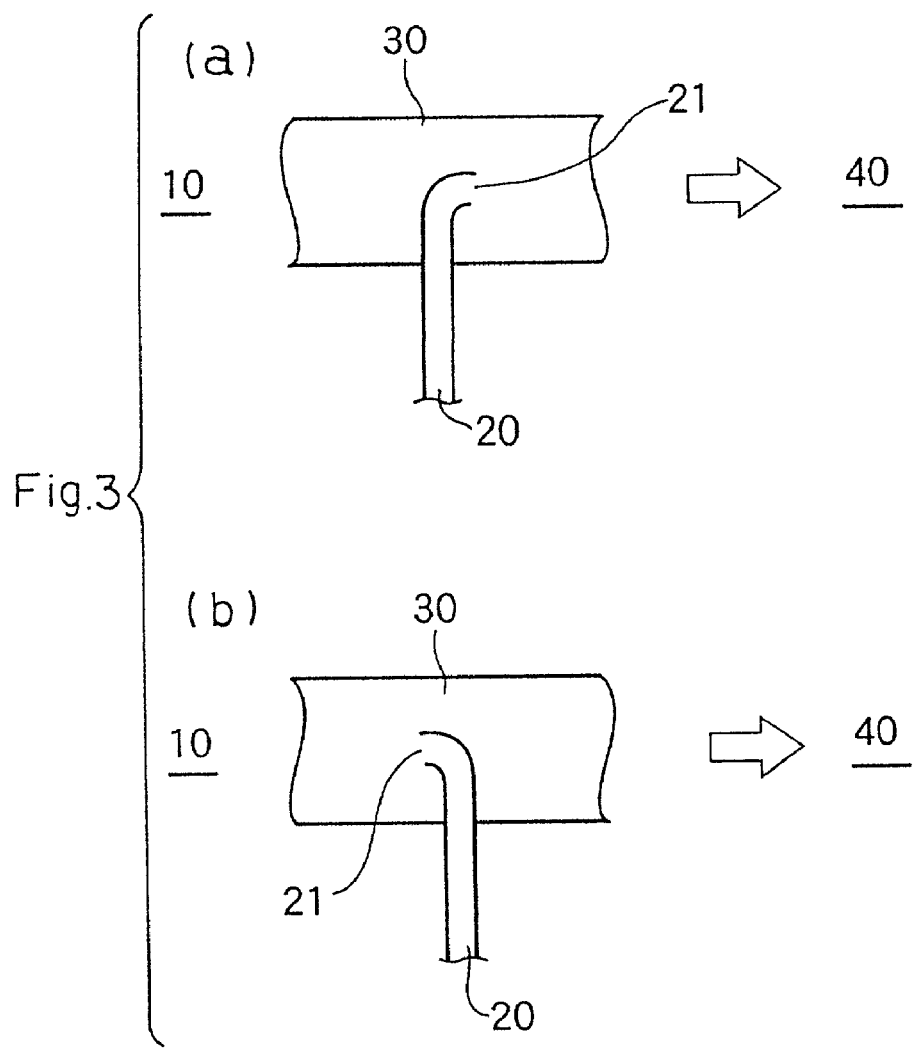
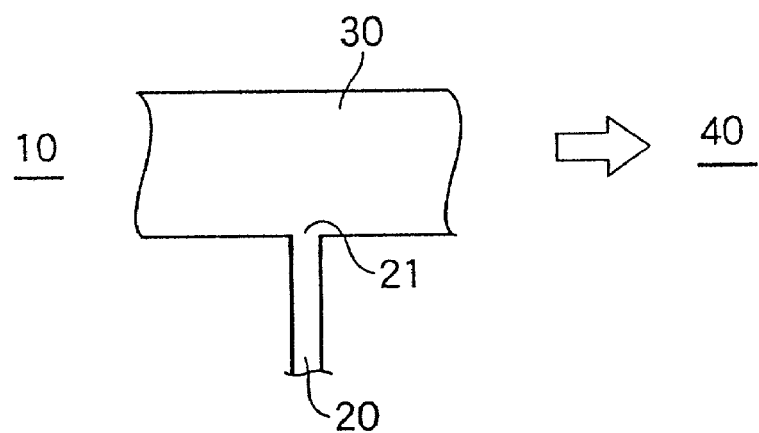

Fig.5
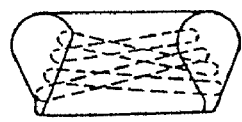
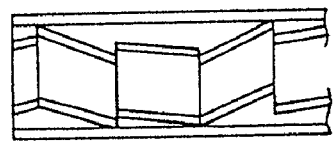
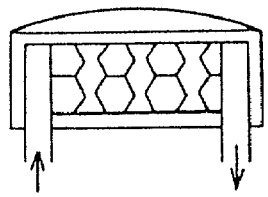
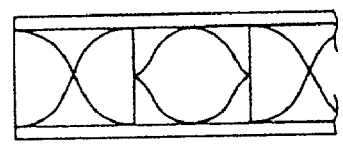
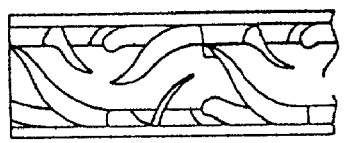
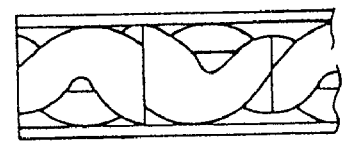
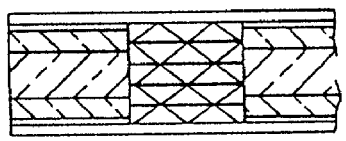
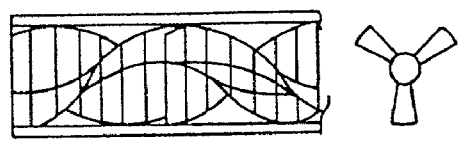
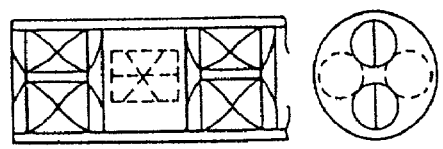
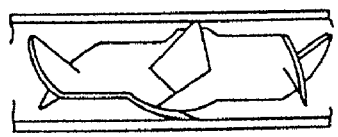
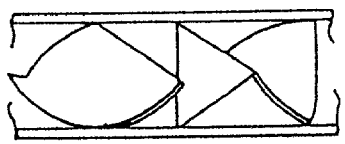

Fig. 8
(a) 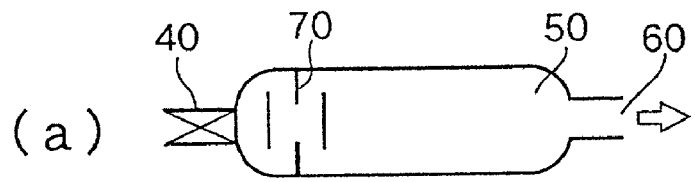
(b) 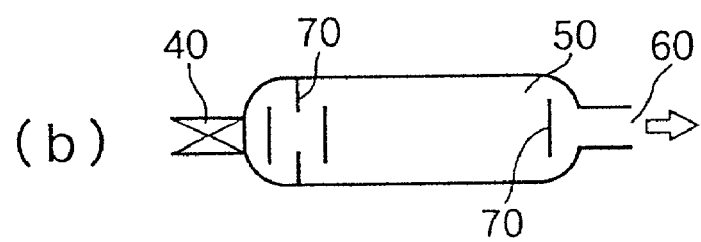
(c) 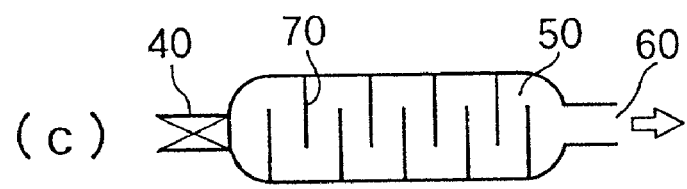
(d) 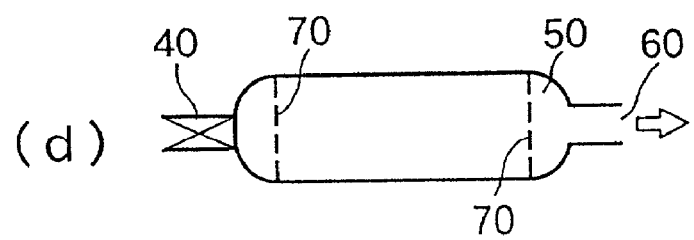
(e) 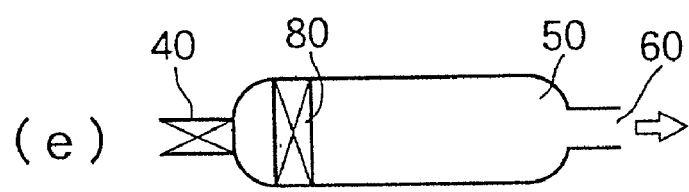
(f) 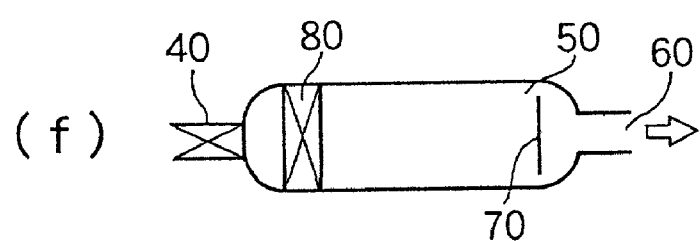

METHOD FOR PURIFICATION OF ACRYLIC ACID

BACKGROUND OF THE INVENTION

A. Technical Field

The present invention relates to a method for purification of a crude acrylic acid, which enables to efficiently eliminate aldehydes, particularly, furfural and/or acrolein, existing as impurities in the crude acrylic acid which is obtained by a vapor phase oxidation of propylene and/or acrolein.

B. Background Art

It is known that aldehyde such as furfural, acrolein, benzaldehyde, and so on and ketone such as acetone are by-produced as impurities in acrylic acid obtained by the vapor phase oxidation of propylene and/or acrolein. These impurities cause problems such as retardation of polymerization rate, decreasing of polymerization degree, coloring of polymers, and so on when acrylic acid is used as a raw material for a high molecular material such as water absorbing resins.

Generally the crude acrylic acid obtained by the vapor phase oxidation process is in general purified by distillation to eliminate impurities and, then, used in various applications. But it is difficult to separate aldehyde from acrylic acid because of close boiling point of acrylic acid and aldehyde such as furfural out of the above-mentioned impurities. For this reason, it is known to treat aldehyde with chemicals such as amine or hydrazine in order to raise boiling point of these aldehyde before distillation.

In order to achieve complete conversion of aldehyde with the aldehyde treatment chemical to form high boiling material, an excess amount of the aldehyde treatment chemical against an amount of aldehyde is used because of an equilibrium established in the reaction of aldehyde and the aldehyde treatment chemical. Also, in order to avoid the regeneration of aldehyde during distillation, distillation should be performed in the presence of a considerable amount of unreacted aldehyde treatment chemical. On the other hand the excess amount of the aldehyde treatment chemical induces polymerization of acrylic acid during distillation, which brings polymer deposit in a distillation column to cause deteriorating of heat transfer efficiency of a reboiler, interfering of distillation performance, and clogging in the distillation column, which may result in plant shut down.

It has been expected to establish the process of purifying acrylic acid to eliminate aldehyde efficiently without polymerization of acrylic acid, and several treatment methods have been proposed such as a method for distillation of the crude acrylic acid in the presence of hydrazine and sulfuric acid as described in JP-A-316027/1997 and a method for distillation of the crude acrylic acid at not more than 100° C. with hydrazine and copper dithiocarbamates as described in JP-A-228548/1995.

Since sulfuric acid and copper dithiocarbamates are used in addition to hydrazine as the aldehyde treatment chemical according to these methods, these material cause problems such as corrosion of metal on inner surface of equipment such as a column and piping. To solve this problem, a corrosion resistant material or anti-corrosive treatment are requested, which increases equipment cost and, hence, production cost. These methods are not industrially easy and economical one.

SUMMARY OF THE INVENTION

A. Object of the Invention

An object of the present invention is to provide an industrially easy and economical method for purification of acrylic acid which enables to efficiently eliminate impurities from a crude acrylic acid containing aldehydes, particularly, furfural and/or acrolein, as the impurities while the formation of acrylic acid polymer is inhibited.

B. Disclosure of the Invention

Extensive study has been made by the present inventors to solve the above-mentioned problems. As a result, it was found that, at a specific range of the concentration ratio of furfural to acrolein, efficiency of the aldehyde treatment chemical is improved and, at successive distillation, impurities are efficiently eliminated. And also the amount of aldehyde treatment chemical to be used can be reduced due to improved efficiency of the aldehyde treatment chemical and, further, polymer formation can be retarded, and, thus, the present invention is established.

That is, a method for purification of acrylic acid, according to the present invention, comprises the step of distilling a crude acrylic acid containing furfural and acrolein as impurities which is charged with an aldehyde treatment chemical, wherein the concentration ratio of furfural to acrolein by weight in the crude acrylic acid is adjusted so as to satisfy the following equation:

$$\text{(furfural concentration by weight)/(acrolein concentration by weight)} \leq 100.$$

These and other objects and the advantages of the present invention will be more fully apparent from the following detailed disclosure.

BRIEF DESCRIPTION OF THE DRAWINGS

FIG. 3 is a view showing two examples of nozzle for charging the aldehyde treatment chemical.

FIG. 4 is a view showing a status of nozzle being not extended to the charging part.

FIG. 5 is a view showing several examples of non-stirring mixers.

FIG. 8 is a view showing several patterns of mixing equipment of the aldehyde treatment chemical having inner devices in the mixing part.

EXPLANATION OF THE SYMBOLS

Figure 1:
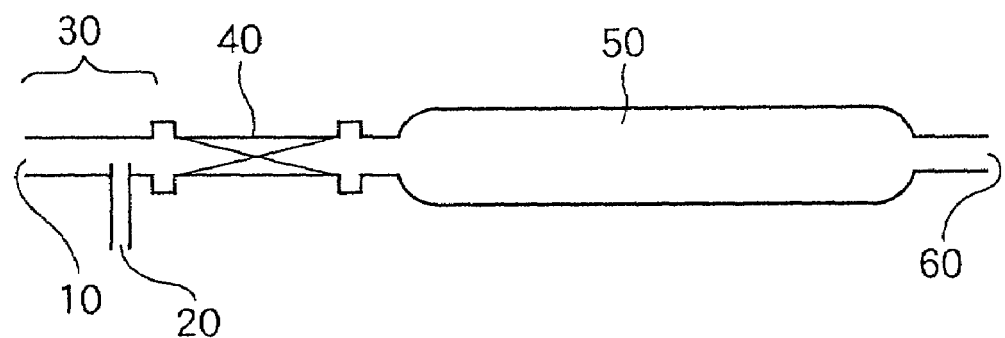
FIG. 1 is a schematic representation of equipment for mixing of the aldehyde treatment chemical to be used preferably for implementing of the present invention.

10 Inlet of the crude acrylic acid
20 Charging portion of the aldehyde treatment chemical
21 Opening of the nozzle
30 Charging part
40 Mixing part
50 Residence part
60 Discharge point of liquid crude acrylic acid
70 Baffle
80 Inside device
110 First step column
111 Crude acrylic acid
112 Aldehyde treatment chemical
120 Second step column
121 Purified acrylic acid
122 Residue liquid
131 Acrylic acid
132 Waste liquid

DETAILED DESCRIPTION OF THE INVENTION

The present invention is described in detail by referring to the following Embodiments.

(Crude Acrylic Acid):

The crude acrylic acid to be used for the present invention is prepared by the vapor phase oxidation process from propylene and/or acrolein and contains impurities by-produced or contaminated in production processes. The above-mentioned impurities are aldehyde such as furfural, acrolein, benzaldehyde and so on and ketone such as acetone. And, further, the present invention specifically provides the method for effective purification of the crude acrylic acid containing specifically furfural and acrolein. Production of acrylic acid by the vapor phase oxidation is not limited, but implemented by the use of prevailed raw materials, reaction processes and process conditions. The crude acrylic acid obtained can be a solution in a solvent such as water.

(Basis of Purification):

According to the present invention, it is important to adjust the concentration ratio of furfural to acrolein by weight in the crude acrylic acid so as to satisfy the following equation:

(furfural concentration by weight)/(acrolein concentration by weight)≦100.

before addition of the aldehyde treatment chemical. Keeping the concentration ratio of furfural to acrolein being 100 or below is not particularly limited, but is preferably adjusted so as to satisfy the following equation:

2≦(furfural concentration by weight)/(acrolein concentration by weight)≦30.

With keeping the concentration ratio of furfural to acrolein within the above range, efficiency of the aldehyde treatment is improved, which enables to eliminate impurities efficiently on distillation. And, further, improved efficiency of the aldehyde treatment chemical allows to decrease an amount of the aldehyde treatment chemical to be used and, as a result, to inhibit polymer formation. In the case where the concentration ratio of furfural to acrolein is more than 100, large excess amount of the aldehyde treatment chemical is required and induces polymer formation during distillation.

According to the present invention, the content of furfural and acrolein in crude acrylic acid is not specifically limited, but a total amount of furfural and acrolein below 5000 ppm by weight is preferable, and below 1000 ppm by weight more favorable.

A method for adjusting the concentration ratio of furfural to acrolein in the crude acrylic acid is practically as follows. To measure each concentration of furfural and acrolein in the crude acrylic acid prepared by the vapor phase oxidation, and, then, to add either furfural or acrolein so as to form a specific ratio of furfural to acrolein, or to control each production step such as oxidation reaction process, light ends cut process, solvent recovery process, heavy ends cut process etc. so as to keep the concentration ratio of furfural to acrolein. Preferably it is adjusted by the latter method, that is, controlling operation condition of each process to produce the crude acrylic acid.

Adjusting the concentration ratio of furfural to acrolein in the crude acrylic acid can be done by increasing or decreasing of concentration of both furfural and acrolein, or by increasing or decreasing a concentration of either furfural or acrolein, but preferably done by acrolein. This is because that acrolein is a raw material component yielding acrylic acid and, further, that each production condition of any process is easily varied due to boiling point of acrolein and acrylic acid being apart. More specifically, for example, for adjusting acrolein concentration by weight on oxidation reaction process, decreasing (or increasing) of reaction temperature brings decreasing (or increasing) of conversion of acrolein to acrylic acid, which results in increasing (or decreasing) of unreacted raw material, acrolein. For adjusting acrolein concentration on light ends cut process and solvent recovery process, for example, decreasing (or increasing) distillation temperature decreases (or increases) a discharge rate of acrolein, which brings increases (or decreases) of acrolein concentration in the crude acrylic acid.

For adjusting acrolein concentration on heavy ends cut process, for example, acrolein is richer than furfural on the top of heavy ends cut column and furfural is richer than acrolein at the middle of the column. Knowing the facts, the concentration ratio of furfural to acrolein is adjusted by selecting a discharge point or by blending a stream from the top and a stream from the middle points at a suitable ratio so as to get a desired ratio of furfural to acrolein.

According to the present invention, the aldehyde treatment chemical is considered such as hydrazine, amine etc., but hydrazine is specifically preferable for a reason such as its efficient performance of eliminating furfural and other reason described hereinafter. As hydrazine, hydrazine hydrate, phenylhydrazine, hydrazine sulfate, hydrazine chloride, are practically considered. And the aldehyde treatment chemical is charged as liquid, but can be as solid such as powder.

The aldehyde treatment chemical to be charged is favorably less than 8.0 mole per 1 mole of furfural in the above-mentioned crude acrylic acid, more favorably less than 6.0 mole, and most favorably less than 4.0 mole. In the case of charging more than 8.0 mole of the aldehyde treatment chemical per 1 mole of furfural in the crude acrylic acid, polymer formation can not inhibited during distillation, which may cause problems such as polymer deposit in the column.

The method for charging the above-mentioned aldehyde treatment chemical is not limited, but can be such method for charging it directly to crude acrylic acid and charging it as a solution using a suitable solvent. With regard to a timing of charging the aldehyde treatment chemical, it can be, for example, preferably charged right after the production of the crude acrylic acid or right before the distillation. Practically it is common practice in industry to charge the treatment chemical dissolved in the crude acrylic acid to be supplied for distillation.

(Reaction Method on Aldehyde Treatment):

According to the present invention, a reaction method on the aldehyde treatment is not limited particularly, and, accordingly, a reaction condition of the above-mentioned aldehyde treatment chemical and the above-mentioned acrylic acid is not limited particularly, but a hydrazine compound as an aldehyde treatment chemical is favorably used for a reason described below by referring Embodiments in detail.

Aldehyde reacts with hydrazine in acrylic acid at low temperature for a certain period of time to form a high boiling compound completely. In addition, the high boiling compound formed does not decompose to regenerate aldehyde with no presence of remaining hydrazine during distillation. Hydrazine tends to decompose thermally, which particularly is accelerated with a temperature increase. Therefore, the aldehyde treatment using hydrazine is preferably done at low temperature for long period or at low temperature for short period, at the beginning, then successively at a elevated temperature. Using this method, aldehyde is completely converted to high boiling compound and an excess hydrazine is decomposed.

In the case using hydrazine as the aldehyde treatment chemical, the concentration of hydrazine remaining after the aldehyde treatment is adjusted to not more than 100 ppm by weight, preferably not more than 80 ppm by weight, and most preferable not more than 10 ppm by weight, because the adjustment of the residual hydrazine concentration to not more than 100 ppm by weight increases the effect of inhibiting the formation of polymers in the distillation step.

Next, it is preferable that the aldehyde treatment is carried out at a temperature of 50° C. or below (more preferably 0 to 50° C., still more preferably 20 to 50° C.) or that, after the treatment at a temperature of 50° C. or below (more preferably 0 to 50° C., still more preferably 20 to 50° C.), the aldehyde is further treated at a temperature of not lower than 60° C. (more preferably 60 to 100° C., still more preferably 60 to 80° C.). The treatment period is well determined by the amount of hydrazine and the treatment temperature, and it is not limited if it is satisfactory with complete treatment of aldehyde to form high boiling material and with a concentration of remaining hydrazine of not more than 100 ppm by weight. However, in the case where the treatment is carried out at a temperature of 50° C. or below, the treatment is preferably carried out for not less than 30 minutes, more preferably not less than 1 hour. In the case where the treatment is carried out at a temperature of 50° C. or below and then further carried out at a temperature of not lower than 60° C., it is preferable that the treatment is carried out for not less than 5 minutes, more preferably not less than 10 minutes at a temperature of 50° C. or below, and then further carried out for not less than 5 minutes, more preferably not less than 10 minutes, at a temperature of not lower than 60° C. Thus, the aldehyde treatment at a low temperature of 50° C. or below for a long period of time, or first at a low temperature of 50° C. or below for a short period of time and then at a high temperature of not lower than 60° C., gives complete conversion of aldehyde to high boiling material together with content of hydrazine remaining being less not more than 100 ppm by weight through decomposition of remaining hydrazine after the treatment.

(Reaction Equipment for Aldehyde Treatment):

Aldehyde treatment is done, for example, in a vessel where the crude acrylic acid and hydrazine are charged for reaction at the above-mentioned temperature and for the above-mentioned treatment period. The treatment is not limited, but, for example, can be done either by batch process or continuous one. But a continuous one is preferable for industry. For continuous one, a good, efficient and uniform mixing of the crude acrylic acid with treatment chemical is preferable.

Then, equipment to perform good mixing and residence is described below.

This vessel is equipped with the inlet of the crude acrylic acid (10) and the charging tube of the aldehyde treatment chemical (20), both of which constitute the charging part (30), the mixing part (40) connecting to the above-mentioned charging part for mixing the crude acrylic acid and the aldehyde treatment chemical and also connecting to a residence part (50), and the residence part (50) connecting to the discharge tube (60).

Figure 2:
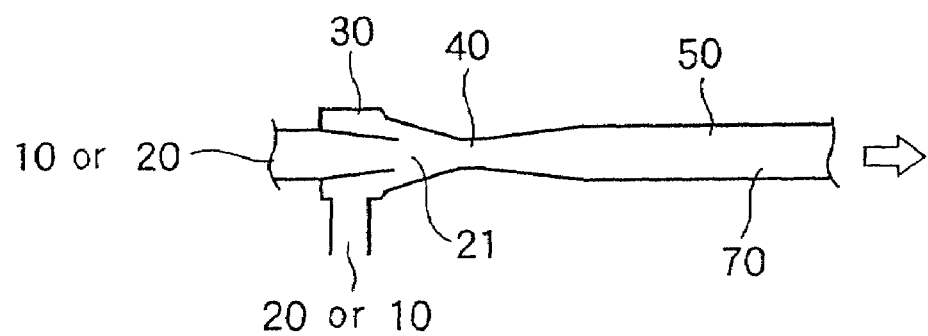
FIG. 2 is a schematic representation of equipment for mixing of the aldehyde treatment chemical equipped with an injector as a charging and mixing parts.

The charging tube of the aldehyde treatment chemical (20) is, for example, a nozzle extended to the charging part (30) as shown in FIG. 1 or a nozzle of so called injector type nozzle as shown in FIG. 2. Either one works for charging the aldehyde treatment chemical into the acrylic acid solution.

In case of using the extended nozzle, an end of the charging tube of the aldehyde treatment chemical (20) which is extended to the charging part (30) is preferably located on the centerline of the charging part (30). With the arrangement of the extended nozzle to the point of the charging part (30) together with a flow of the acrylic acid to be supplied, the mixing of the crude acrylic acid and the aldehyde treatment chemical is well achieved. Moreover, a cross section of the charging part is not limited to circular, but can be a tube of multiple-angle shape such as a triangle or a square one.

In the case where the charging tube (20) is an extended nozzle, the opening end (21) of the charging tube (20) is preferably directed to the inlet tube (10) as shown in FIG. 3 (*a*) or to the mixing part (40) as shown in FIG. 3 (*b*). Flow of the aldehyde treatment chemical through the above-mentioned nozzle runs along to that of the acrylic acid or to the mixing part (40) or hits together, which increases a mixing efficiency. Contrary the flow can be at a right angle, but the position of the opening end (21) is preferable at the center line of the charging part (30) even in this case.

Also, the number of the opening end is not limited as one, but can be multiple ones.

In the case where the opening end of the nozzle (21) is not extended to the charging part (30) as shown in FIG. 4, the mixing of the liquids is effectively achieved by adjusting an area of a cross section of the opening end of the nozzle and a flow rate of the aldehyde treatment chemical against a flow rate of the crude acrylic acid so as to avoid an contacting of the aldehyde treatment chemical to an inner surface of the mixing part (40), which bring good mixing without problem.

Using this mixing equipment having the mixing part (40) of mixing the crude acrylic acid and the aldehyde treatment chemical, the crude acrylic acid is charged through the inlet (10) of the charging part (30) and flow into the mixing part (40) with the aldehyde treatment chemical. Accordingly, the above-mentioned mixing part (40) is designed to be connected to the charging part (30), but a shape of a connection is not limited as a round one.

A distance between the inlet of the aldehyde treatment chemical (20) in the charging part (30) and an inlet of the above-mentioned mixing part (40) is not limited, but the distance is preferably 0.1 to 5.0 times of the inside diameter of the charging part, more preferably 0.2 to 3.0 times, and most preferably 0.3 to 2.0 times. In the range of this distance, a flow of crude acrylic acid causes a turbulent one to bring a quite efficient mixing. A ratio of the distance of less than 0.1 makes fabrication difficult and that of more than 5.0 gives insufficient result. "Inside diameter" as shown below in an equation is calculated as an equivalent inside diameter for the case where a cross-sectional shape of the charging part (30) is not round. Using the equation below, the distance is favorably elucidated for the charging part (30) of not-round shape. Further, in the case of using an injector inlet for the aldehyde treatment chemical, a suitable distance from a charging point of the crude acrylic acid to a charging point of the mixing part is estimated. In the case where an inside diameter of the charging part is not uniform, the minimum diameter or an equivalent diameter of the charging part is preferably used for distance calculation.

Equivalent inside diameter=4×(cross section area of the charging part)/(inside periphery length of the charging part)

Figure 6:
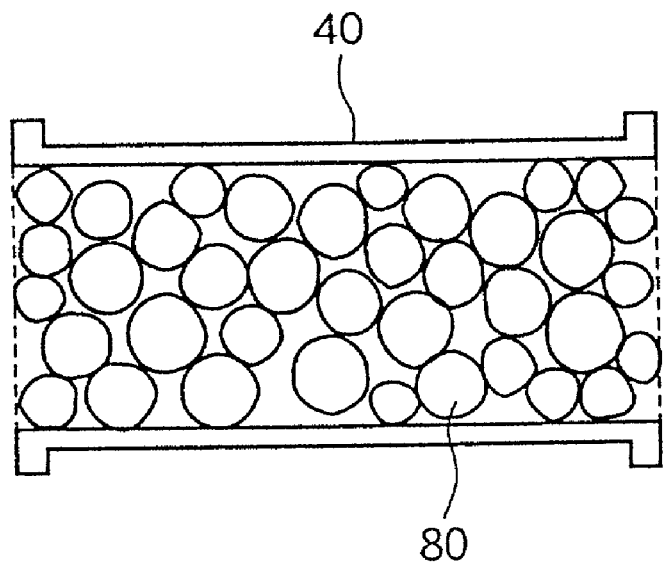
FIG. 6 is a view showing an example of the mixing part with two perforated plates and spherical materials between the plates.

This mixing part (40) is preferably a non-stirring type mixer. Here, the non-stirring type mixer means a mixer to mix multiple fluids with energy of fluids without mechanical motion such as static mixers with several shapes and baffles shown in FIG. 5 and an injector type flow mixers as in FIG. 2. As to a non-stirring mixer, it is not limited as those shown in FIG. 5, but any type or any combination of packings, or plates to be used for distillation, perforated plates, and spheres is used. FIG. 6 shows an example of having perforated plates at both and packed with spheres between the plates. The non-stirring mixer provides uniform mixing without additional energy expense, and decreases an amount of the aldehyde treatment chemical. This method can adopt any of known non-stirring mixers.

For non-stirring mixer, a length of the above-mentioned mixing part (40) is 2 to 35 times of inside diameter of the above-mentioned mixer, more preferably 4 to 25 times, and most preferably 6 to 20 times. At a predetermined flow rate of the crude acrylic acid, the value described above of less than 2 times results in poor mixing and that more than 35 does not make any improvement of mixing.

Figure 7:
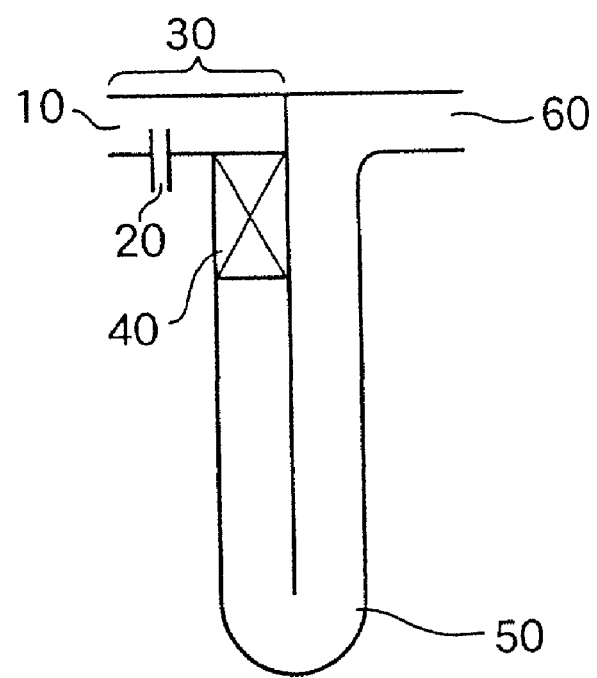
FIG. 7 is a schematic representation of mixing equipment of the aldehyde treatment chemical with vertical layout of the mixing part.

Connection of the mixing part (40) to the charging part (30) is not limited as horizontal as shown in FIG. 1, but can be vertical as shown in FIG. 7. With a vertical lay out of the mixing parts, a mixture of the crude acrylic acid and the aldehyde treatment chemical can be charged from the top of the mixer or from the bottom as shown in FIG. 7. There is no restriction on layout and flow direction. In addition, the mixing part (40) can be places not only horizontally or vertically, but also slantingly, and also of bending shape.

In the case where the charging tube of the aldehyde treatment chemical is the above-mentioned injector type shown in FIG. 2, it functions as the injector (20) and as the mixer (40). Therefore, clear definition is not necessarily required from structure point for the charging part (30), the mixing part (40), and the residence part (50). And the equipment serving as a function of charging the aldehyde treatment chemical, mixing of both liquids, and residence is enough practically. More specifically for example, FIG. 2 shows the charging part (30) having an opening of the inlet tube of the crude acrylic acid (10) or that of the charging tube of the aldehyde treatment chemical (20), at a position shown as numeral 21, a successive connecting most narrow part (30) serving as a mixer (40), and a next successive portion serving as a residence part (50).

The residence part (50) of this equipment has a space to keep a liquid of the crude acrylic acid and the aldehyde treatment which was mixed at the mixing part (40) for at a specific period of time and is required to have at least one of the discharge tubes of the liquid mixture (60). In general, the discharge tube (60) is connected to the purification column.

The residence part (50) is designed as that a maximum cross section area of the residence part (50) being preferably 2 to 500 times of that of the inlet tube of the crude acrylic acid (10) at the charging part (30), more preferably 20 to 400 times, most preferably 50 to 200 times, to keep the liquid mixture for a specific period. Enough reaction time for the crude acrylic acid and the aldehyde treatment chemical ensures increasing of aldehyde treatment. The above-mentioned value of less than 2 times requests the residence part (50) of longer length to ensure an enough reaction time, which unfavorably brings an increased pressure drop. On the other hand, that of more than 500 brings an unbalanced flow in the residence part (50), which results in non-uniform mixing and residence time.

Once non-uniform flow in the residence part (50) even within the above-mentioned range, a case of non-uniform residence time happens, accordingly the equipment is preferably attached with an internal device to secure a uniform flow. Such internal device is, for example, a plate, sphere, wire-mesh and sheet. Example of plate is a baffle plate. And the baffle may have hole more than one, which allow the liquid mixture pass through. Also, the device is a static mixer or packings for distillation column.

This internal device is placed at any place in the residence part (50), but preferably placed to closer position to the inlet side of residence part so as to secure a uniform residence time. Examples of such residence part with the device are shown in FIG. 8. As shown, (a) shows multiple baffles (70) placed only to the inlet or (b) does the baffles (70) close to the discharge tube (60). Also (c) shows baffles (70) placed uniformly throughout the residence part (50). Plates having multiple holes are used as the baffles (70) and placed close to both the inlet and the discharge tube of the residence part (50) as shown in(d). Further, the inside device (80) such as sphere, available random packings, available wire-mesh, sheet of structured packings and so on is placed at a place of the residence part (50) as shown in (e) and additional baffles (70) are placed near the exit tube (60) as shown in (f). Sometimes, the internal device in the residence part is bulky, which results in increase of the size of the residence part in order to secure enough residence time. Then, it is preferable to attach at limited portion.

Figure 9:
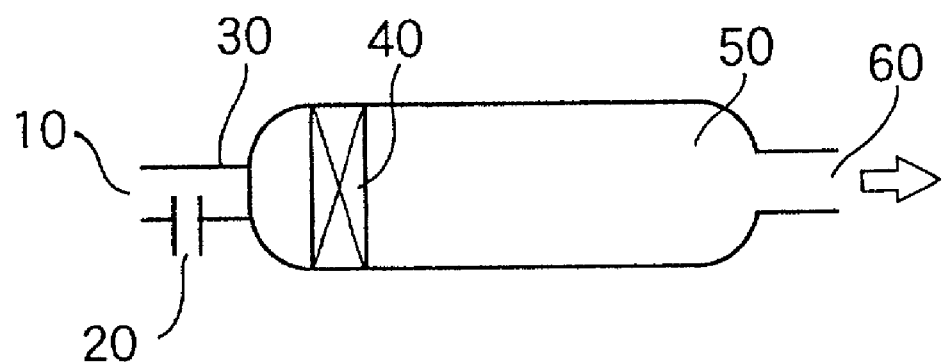
FIG. 9 is a schematic representation of mixing equipment of the aldehyde treatment chemical with different tube in inside diameter for the mixing and residence parts.
Figure 10:
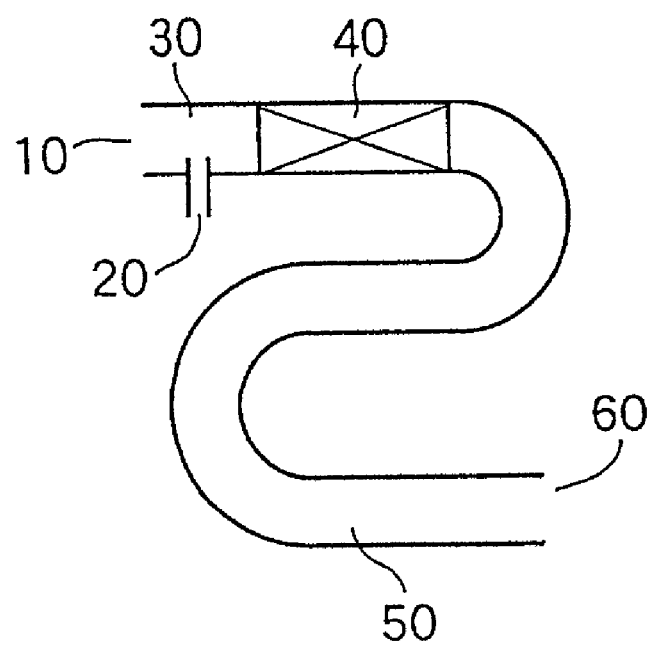
FIG. 10 is a schematic representation of mixing equipment of the aldehyde treatment chemical with zigzag residence part.
Figure 11:
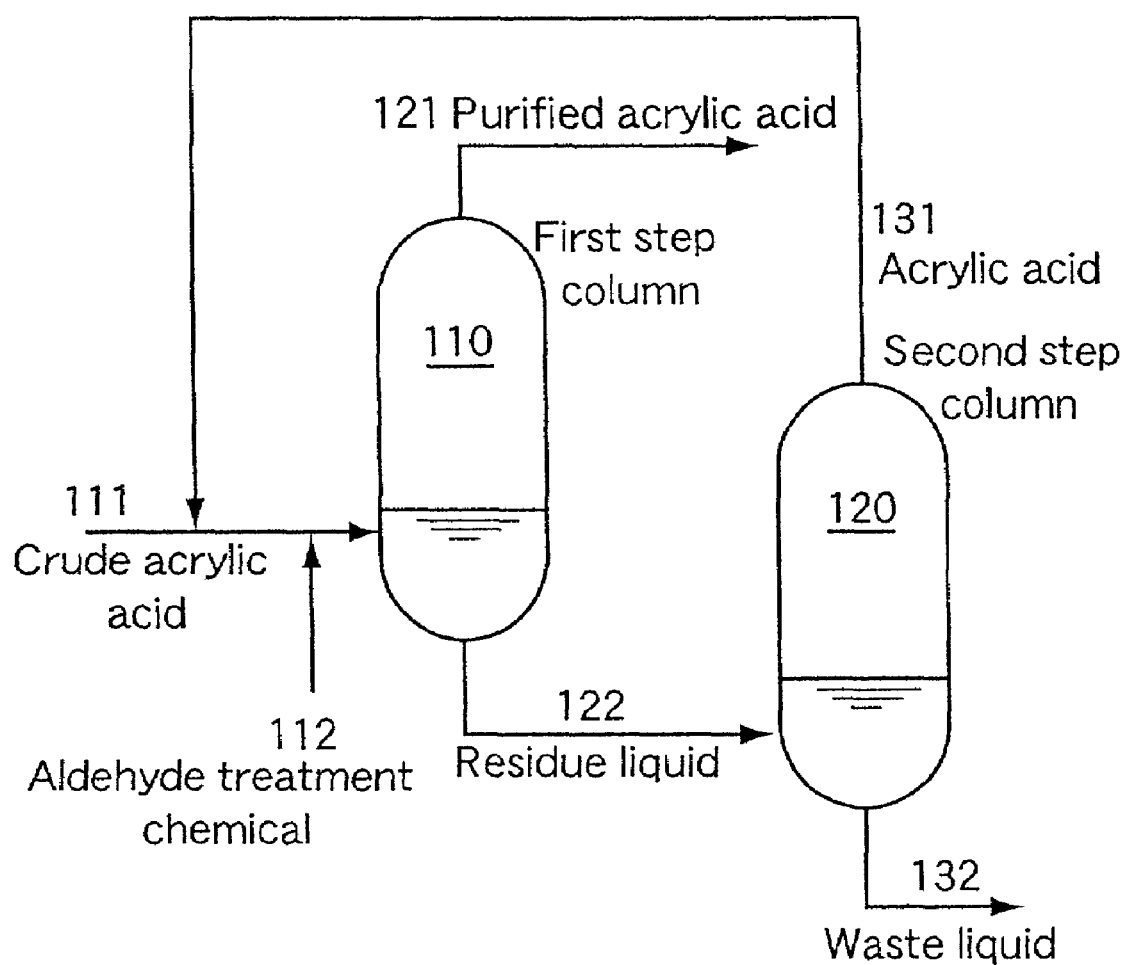
FIG. 11 is a block diagram showing layout of the treatment equipment by which the two step distillation method is carried out.

The shape of the residence part (50) having above volume is not limited, but preferably a cylinder, which allow an easy installation of the internal device. In this case, a diameter of the residence part can be different from that of the mixing part (40) as shown in FIG. 1, or same to as shown in FIG. 9. Also, the residence part (50) can be bent or zigzagged, and also with different sizes in the inside diameter at portions throughout the residence part as in FIG. 10.

When adding the aldehyde treatment chemical to the crude acrylic acid, a charging linear velocity of the aldehyde treatment chemical against that of the crude acrylic acid is preferably in a range of 0.05 to 5.0 times for easy mixing of two liquids, more preferably 0.1 to 3.0 times, and most preferably 0.2 to 1.5 times. With this value of less than 0.05 times, the opening of inlet tube is required to be larger to achieve suitable charging of the aldehyde treatment chemical. On the other hand, with that of more than 5.0 times, the aldehyde treatment chemical charged passes through a flow of the crude acrylic acid. Both cases cause insufficient mixing.

(Rectification):

According to the present invention, distillation method is not limited, but can be various one, for example, flash distillation, rectification and so on. The above-mentioned distillation can be batch or continuous one, but industrially continuous one is preferable. In regard to equipment, existing equipment is satisfactorily used. Practically, for example, flash column, random packing column, structured packing column, bubble cap tray column, valve tray column, sieve tray column, and dual-flow tray column is used.

Distillation condition is not limited particularly, but practically a residence time of 0.5 to 20 hours, preferably 1 to 15 hours, and a distillation temperature of 40 to 100° C. (preferably 50 to 100° C.), a concentration ratio of 4 to 100 times are adopted. During distillation, well-known polymerization inhibitors can be charged. Polymerization inhibitor is phenol such as phenol, hydroquinone, methoquinone, catechol, cresol etc. Its amount is not limited, but commonly favorable in the range of 1 to 1000 ppm, and more favorable in the range of 10 to 500 ppm to the acrylic acid.

Distillation method can be two step distillations.

<First Step of Distillation>

A treated solution obtained by the crude acrylic acid with the aldehyde treatment chemical is charged to the first column and discharge acrylic acid from the top of the column.

Acrylic acid distillate contains very low concentration of impurities, practically highly pure acrylic acid with no impurities.

At the bottom of the column, a liquid remaining after distillation is called as a residue, which contains remaining acrylic acid and impurities, and also products from the reaction of the aldehyde treatment chemical with aldehyde. And it may contain unreacted aldehyde treatment chemical.

Operation condition of the first column is set for distilled off of acrylic acid distillate, for instance, a bottom temperature of 50 to 70° C., a residence time of the bottom residue of 1 to 2 hours, and a concentration ratio of 4 to 25 times are preferably suggested. The concentration ratio is a ratio of a charged amount to the first column per a discharge amount of the bottom residue.

Decreasing the bottom temperature comparatively and shortening the residence time reduces polymer formation and, also, decomposition of the reaction product of the aldehyde treatment chemical with aldehyde. With low concentration ratio, the distillate acrylic acid has a low possibility of containing impurities and, contrarily, the residue contains high concentration of acrylic acid.

<Second Step of Distillation>

Basic structure of this column is same to the first column. A distillation column with decomposition can be used. A distillation column with decomposition of recovering acrylic acid from decomposition of acrylic acid dimmer is not limited specifically, for example preferably such as a column having a thermal decomposition vessel and recovering equipment. The second step column receives the residue at the bottom of the first column, and distillate off to recover acrylic acid from the top of the column after heating the residue from the first column. Unreacted aldehyde treatment chemical and aldehyde as residue at the first column reacts in the second step column, which is separated from acrylic acid.

Recovered distillate of highly pure acrylic acid, if it being to meet a spec, is transferred to the distillate from the first step column for use. With the residue containing impurities of more than spec, a distillate is sent to the first column repeatedly for distillation.

The residue at the bottom of the second column containing the reaction product of the aldehyde treatment chemical and aldehyde and an excess amount of the aldehyde treatment chemical is discharged for waste or recover useful materials for reuse.

Operation condition of the second column is set so as to perform distillation of acrylic acid. In practice, a temperature of the bottom liquid of 80 to 100° C., a residence time of the residue of 10 to 20 hours, concentration ratio of 10 to 30 times are preferable.

According to the two step method, a treated liquid highly containing the aldehyde treatment chemical is firstly distilled off at the first step column at comparatively low temperature with short residence time and low concentration ratio, which contains lesser amount of aldehyde treatment chemical and is distilled at the second column. The treatment at the second step column with lesser amount of the aldehyde treatment chemical is done at the second step column under increased retardation of acrylic acid polymerization.

FIG. 12 shows a flow of treatment for the two step distillation.

The crude acrylic acid 111 charged with the aldehyde treatment chemical 112 is charged to a lower position of the first step column 110. The crude acrylic acid 111 containing the aldehyde treatment chemical 112 is heated in the first column 110 to obtain a purified acrylic acid 121 at the top of the column. From the bottom of the first step column, the residue liquid 122 is discharged.

The discharged residue liquid 122 is charged to a lower portion of the second step column 120 for heating. The acrylic acid in the residue liquid 122 is distilled from the top of the second step column 120 and the distillate acrylic acid 131 is transferred again to the first step column 110.

Accordingly, the first step column 110 is charged with the crude acrylic acid 111 and the aldehyde treatment chemical 112, and also acrylic acid 131 from the second step column.

From the bottom of the second step column 120, the waste liquid 132 after separation of acrylic acid is discharged.

(Effects and Advantages of the Invention):

According to the present invention, impurities are efficiently eliminated from the crude acrylic acid containing furfural and acrolein as impurities industrially with easiness and reasonable cost under inhibiting of polymer formation.

DETAILED DESCRIPTION OF THE PREFERRED EMBODIMENTS

Hereinafter, the present invention is more specifically illustrated by the following examples of some preferred embodiments in comparison with comparative examples not according to the invention. However, the invention is not limited to the below-mentioned examples.

Incidentally, hereinafter, the contents of furfural and acrolein were measured by gas chromatography under conditions shown below.

| Column: | capillary column |
|---|---|
|  | (J & W Co., DB-WAX 30 m × 0.53 ID 1 μm) |
| Carrier gas: | He (0.5 kg/cm$^2$) |
| Injection temperature: | 250° C. |
| Detector temperature: | 250° C. |
| Column temperature: | 50 to 220° C. (10° C./min.) |

And remaining hydrazine content was measured as described below:

1 ml. of a sample and 40 ml. of 0.1% by weight of p-dimethyl, aminobenzaldehyde (solvent; 10% by volume of ethanol containing HCl was mixed in a brawn beaker, left at 25° C. for 10 minutes and then measured 458 nm absorbance by a UV spectrometer.

EXAMPLE 1

Acrolein was charged to the crude acrylic acid containing 300 ppm by weight of furfural and 2 ppm by weight of acrolein as impurities so as to get an adjusted acrylic acid containing 100 ppm by weight of acrolein. The adjusted acrylic acid was charged with hydrazine hydrate at a ratio of 3.0 mole per 1 mole of furfural and, then, distilled continuously using a packed column. During continuous distillation, 99% of fed material was discharged continuously as a distillate and a part of the distillate was recycled to the top of the column as a reflux liquid at a reflux ratio of 0.3. In addition, methoquinone as a polymerization inhibitor dissolved in the recycle stream was charged to the column at a ratio of 10 ppm by weight per material to be fed.

The distillate obtained was found containing less than 0.5 ppm of both furfural and acrolein in purified acrylic acid. After 24 hour continuous distillation and normal shut down, inspection of the column showed no deposit of acrylic acid polymer in the column.

EXAMPLES 2 TO 4

Distillation was repeated in the same manner as in Example 1 except using various concentrations by weight of acrolein as shown in Table 1, which were prepared by charging acrolein to the crude acrylic acid containing 300 ppm by weight of furfural and 2 ppm by weight of acrolein as impurities.

Furfural and acrolein concentration in purified acrylic acid are shown in Table 1, respectively. After 24 hours continuous distillation and normal shut down, inspection of the column showed no deposit of acrylic acid polymer in the column.

Comparative Example 1

Distillation was repeated in the same manner as in Example 1 except using the crude acrylic acid containing 300 ppm by weight of furfural and 2 ppm by weight of acrolein as impurities without any addition of acrolein.

Distillate obtained showed less than 0.5 ppm of acrolein concentration by weight, but 14 ppm by weight of furfural. Long-term continuous distillation was not performed because of high furfural concentration and insufficient elimination of aldehyde.

Comparative Example 2

Purification was done in the same manner as in Comparative Example 1 except for using 10 mole of hydrazine hydrate per 1 mole of furfural.

Distillate obtained showed less than 0.5 ppm of acrolein and furfural, respectively. But long-term continuous distillation was interrupted after 12 hours elapsed due to flooding. After distillation was stopped, inspection of inside of the distillation column showed acrylic acid polymer deposited heavily in the column.

TABLE 1

|  | Crude acrylic acid | | | Distillate | | | |
|---|---|---|---|---|---|---|---|
|  | Furfural concentration ppm by weight | Acrolein concentration ppm by weight | Concentration ratio of furfural/acrolein by weight | Charged hydrazine (mole) per mole of furfural | Furfural concentration ppm by weight | Acrolein concentration ppm by weight | Polymer formation during distillation |
| Example 1 | 300 | 100 | 3 | 3.0 | Not more than 0.5 | Not more than 0.5 | None |
| Example 2 | 300 | 200 | 1.5 | 3.0 | 0.9 | 0.9 | None |
| Example 3 | 300 | 12 | 25 | 3.0 | Not more than 0.5 | Not more than 0.5 | None |
| Example 4 | 300 | 4 | 75 | 3.0 | 0.7 | Not more than 0.5 | None |
| Comparative Example 1 | 300 | 2 | 150 | 3.0 | 14 | Not more than 0.5 | No long-term operation |
| Comparative Example 2 | 300 | 2 | 150 | 10.0 | Not more than 0.5 | Not more than 0.5 | Heavy formation |

EXAMPLE 5

The crude acrylic acid containing 300 ppm by weight of furfural and 12 ppm by weight of acrolein as impurities was obtained by adjusting the reaction temperature in the oxidation reaction during production of the crude acrylic acid. The crude acrylic acid was charged to equipment shown in FIG. 1 at a flow rate of 1.7 m/s through a pipe having a diameter of 25 mm, to which hydrazine hydrate was charged in the ratio of 3.0 molar times of furfural at a flow rate of 0.2 m/s. An end of nozzle for charging the above-mentioned hydrazine hydrate had a hole of 0.8 mm in diameter to a downstream side at the center of the tube for charging the crude acrylic acid, where a distance to a static mixer was 30 mm. The charging part was, to a downstream side, connected to a Kenics type static mixer of a 275 mm length and the same inside diameter as the charging part, which was, further to a downstream side, connected to the residence part of an inside diameter of 300 mm and of 6000 mm length, a cylinder. (Residence time was about 9 minutes). The residence part was equipped with perforated plates of 300 mm diameter and of 10% opening area at both ends as shown in FIG. 12. Distillation column of 2000 mm in diameter with 5 plates, a discharge line at the top, and a raw material charge line and a bottom liquid discharge line at the bottom was operated at a temperature of 65° C. at the top, a 53 hPa pressure at the top, with a reflux ratio of 0.3, and a purified acrylic acid discharge at 2850 kg/hr. During distillation, a polymerization inhibitor of methoquinone dissolved in a reflux distillate was charged into the column in the ratio of 50 ppm by weight of the charged liquid, and further, oxygen was introduced into the column from its bottom in the ratio of 0.3% by volume of the acrylic acid distillate.

Incidentally, analysis of hydrazine in the crude acrylic acid showed a remaining hydrazine of 150 ppm by weight.

Also, furfural and acrolein in the purified acrylic acid were 0.2 ppm by weight and not more than 0.1 ppm by weight, respectively.

And after stable operation of two months, acrylic acid polymer etc. of 10 kg was found by an inspection of an inside of the column.

EXAMPLE 6

Example 5 was repeated except that the crude acrylic acid preheated, cylinder (residence time: about 40 min.) of 350 mm in diameter and of 20000 mm in length, and having an outside jacket to keep the residence part at a temperature of 40° C. were used. Remaining hydrazine, to be charged to the distillation column, in the crude acrylic acid was 50 ppm by weight.

Furfural and acrolein in the purified acrylic acid were 0.2 ppm by weight and not more than 0.1 ppm by weight, respectively.

And after stable operation of two months, acrylic acid polymer etc. of 3 kg was found by an inspection of the inside of the column.

EXAMPLE 7

Example 5 was repeated except that distillation temperature at the bottom of 60° C., the residence time setting at the bottom as liquid of 1.5 hr, a continuous discharge of a distillate being at 80% of charging acrylic acid (first step distillation), a continuous charging of a stream from the bottom of the first step column to the second column, a temperature at the second step column bottom of 90° C., the residence time setting at the bottom as liquid of 15 hr, a continuous discharge of a distillate being at 90% (second step distillation), a continuous charging of a stream from the bottom of the first step column to the second column, and the crude acrylic acid before the aldehyde treatment being charged with the distillate are used.

Example 5 was repeated except that a column of 900 mm in diameter was used for the second column. Also, Example 5 was followed for the column top pressure, reflux ratio, amount of inhibitor etc.

Furfural and acrolein in the purified acrylic acid from the top of the first step column were 0.2 ppm by weight and not more than 0.1 ppm by weight, respectively.

And after stable operation of two months, acrylic acid polymer etc. was 3 kg in the first step column and no polymer deposit in the second step column was found by an inspection of the inside of the column.

EXAMPLE 8

Example 7 was repeated except that a cylinder (residence time : about 40 min.) of 350 mm in diameter and of 20000 mm in length, and having an outside jacket to keep the residence part at a temperature of 40° C. was adopted.

Furfural and acrolein in the purified acrylic acid from the top of the first step column were 0.2 ppm by weight and not more than 0.1 ppm by weight, respectively.

And after stable operation of two months, acrylic acid polymer etc. was 1 kg in the first step column and no polymer in the second step column was found by an inspection of the inside of the column.

EXAMPLE 9

Same distillation of Example 5 was repeated except that, hydrazine hydrate, was charged through the aldehyde treatment chemical charging tube as shown in FIG. 7, directly to the residence part.

Furfural and acrolein in the purified acrylic acid were 0.4 ppm by weight and not more than 0.1 ppm by weight, respectively.

And after stable operation of two months, acrylic acid polymer etc. was 10 kg in the distillation.

The concentration ratio of furfural to acrolein can be adjusted so as to satisfy any one of the following equations:

$$3 \le \text{(furfural concentration by weight)/(acrolein concentration by weight)} \le 100; \qquad a$$

or $$3 \le \text{(furfural concentration by weight)/(acrolein concentration by weight)} \le 30. \qquad b$$

One method for purification of acrylic acid according to the present invention includes the steps of providing a crude acrylic acid containing furfural and acrolein as impurities, determining a ratio of a concentration of furfural to a concentration of acrolein, determining whether the ratio of the concentration of furfural to the concentration of acrolein is within a preset range and, if so, continuing with said method, determining whether the ratio of the concentration of furfural to the concentration of acrolein is outside said preset range and, if so, adjusting the ratio of the concentration of furfural to the concentration of acrolein to fall within said preset range, charging said crude acrylic acid with a chemical that treats aldehydes, with said step of charging taking place after said steps of determining and after said step of adjusting, and then distilling said crude acrylic acid having said chemical that treats aldehydes while inhibiting formation of acrylic acid polymers.

A present method for purification of acrylic acid includes the steps of a) providing a crude acrylic acid having a concentration ratio of furfural to acrolein by weight that is adjusted so as to satisfy the following equation:

3≦(furfural concentration by weight)/(acrolein concentration by weight)≦100;

then b) charging the crude acrylic acid with an aldehyde treatment chemical, with the aldehyde treatment chemical comprising a hydrazine compound; then c) reacting the hydrazine compound with aldehydes of the crude acrylic acid such that, after said step of reacting and prior to a step of distilling the crude acrylic acid, a concentration of said hydrazine compound in said crude acrylic acid is not more than 100 ppm by weight; and then d) distilling e the crude acrylic acid containing said furfural and acrolein as impurities.

Various details of the invention may be changed without departing from its spirit not its scope. Furthermore, the foregoing description of the preferred embodiments according to the present invention is provided for the purpose of illustration only, and not for the purpose of limiting the invention as defined by the appended claims and their equivalents.

What is claimed is:

1. A method for purification of acrylic acid, which comprises the steps of:
    a) providing a crude acrylic acid having a concentration ratio of furfural to acrolein by weight that is adjusted so as to satisfy the following equation:

3≦(furfural concentration by weight)/(acrolein concentration by weight)≦100;

then
    b) charging the crude acrylic acid with an aldehyde treatment chemical, with the aldehyde treatment chemical comprising a hydrazine compound; then
    c) reacting the hydrazine compound with aldehydes of the crude acrylic acid such that, after said step of reacting and prior to a step of distilling the crude acrylic acid, a concentration of said hydrazine compound in said crude acrylic acid is not more than 100 ppm by weight; and then
    d) distilling the crude acrylic acid containing said furfural and acrolein as impurities.

2. A method according to claim 1, wherein the concentration ratio of furfural to acrolein by weight in said crude acrylic acid is adjusted so as to satisfy the following equation:

3≦(furfural concentration by weight)/(acrolein concentration by weight)≦30.

3. A method according to claim 2, wherein the amount of said aldehyde treatment chemical is not more than 8.0 mole per mole of furfural existing in said crude acrylic acid.

4. A method according to claim 1, wherein the amount of said aldehyde treatment chemical is not more than 8.0 mole per mole of furfural existing in said crude acrylic acid.

5. A method for purification of acrylic acid, comprising the steps of:
    a) providing a crude acrylic acid containing furfural and acrolein as impurities;
    b) determining a ratio of a concentration of furfural to a concentration of acrolein;
    c) determining whether the ratio of the concentration of furfural to the concentration of acrolein is within a preset range and, if so, continuing with said method;
    d) determining whether the ratio of the concentration of furfural to the concentration of acrolein is outside said preset range and, if so, adjusting the ratio of the concentration of furfural to the concentration of acrolein to fall within said preset range;
    e) charging said crude acrylic acid with a chemical that treats aldehydes and selecting, as said chemical that treats aldehydes, a hydrazine compound, with said step of charging taking place after said steps of determining and after said step of adjusting and prior to a step of distilling said crude acrylic acid; then
    f) reacting the hydrazine compound with aldehydes of the crude acrylic acid such that, after said step of reacting and prior to a step of distilling the crude acrylic acid, a concentration of said hydrazine compound in said crude acrylic acid is not more than 100 ppm by weight; and then
    g) distilling said crude acrylic acid.

6. A method according to claim 5, wherein said preset range is: (furfural concentration by weight)/(acrolein concentration by weight)≦100.

7. A method according to claim 5, wherein said preset range is: 2≦(furfural concentration by weight)/(acrolein concentration by weight)≦30.

8. A method according to claim 5, wherein said preset range is: 3≦(furfural concentration by weight)/(acrolein concentration by weight)≦100.

9. A method according to claim 5, wherein said preset range is: 3≦(furfural concentration by weight)/(acrolein concentration by weight)≦30.

10. A method of claim 5, and further comprising the step of selecting an amount of said chemical that treats aldehydes to be not more than 8.0 moles per mole of furfural in said crude acrylic acid.

* * * * *